United States Patent
Binnig et al.

(10) Patent No.: US 10,621,307 B2
(45) Date of Patent: Apr. 14, 2020

(54) IMAGE-BASED PATIENT PROFILES

(75) Inventors: Gerd Binnig, Kottgeisering (DE);
Guenter Schmidt, Munich (DE);
Markus Rinecker, Munich (DE)

(73) Assignee: Definiens GmbH, Munich (DE)

( * ) Notice: Subject to any disclaimer, the term of this patent is extended or adjusted under 35 U.S.C. 154(b) by 1968 days.

(21) Appl. No.: 12/799,709

(22) Filed: Apr. 29, 2010

(65) Prior Publication Data

US 2011/0268331 A1 Nov. 3, 2011

(51) Int. Cl.
*G16H 40/63* (2018.01)
*G06F 19/00* (2018.01)

(52) U.S. Cl.
CPC ........ *G06F 19/3481* (2013.01); *G06F 19/321* (2013.01); *G16H 40/63* (2018.01)

(58) Field of Classification Search
USPC ................................. 382/128–134
See application file for complete search history.

(56) References Cited

U.S. PATENT DOCUMENTS

| | | | | |
|---|---|---|---|---|
| 2005/0136509 A1* | 6/2005 | Gholap | ............... | G01N 33/5091 435/40.5 |
| 2006/0274928 A1* | 12/2006 | Collins | .................... | A61B 6/00 382/132 |
| 2007/0156453 A1* | 7/2007 | Frielinghaus | .......... | A61N 5/103 705/2 |
| 2008/0260218 A1* | 10/2008 | Smith | .................. | A61B 5/0077 382/128 |
| 2008/0260226 A1* | 10/2008 | Moriya | ................ | G06K 9/6201 382/128 |
| 2010/0191541 A1* | 7/2010 | Prokoski | .............. | A61B 5/0064 705/2 |

* cited by examiner

*Primary Examiner* — Rachel L. Porter
(74) *Attorney, Agent, or Firm* — Imperium Patent Works; Darien K. Wallace

(57) ABSTRACT

A system for generating image-based patient profiles acquires digital images from tissue samples and CT and MRI scans. The system detects objects within the images, measures values related to the detected objects, and displays the measured values in patient profile lists that indicate the normal ranges for measured values. The system indicates which measured values fall outside the normal ranges and navigates the user to the objects in the images associated with the abnormal values when the user selects a measured value in the patient profile. Various risks of the existence of different diseases and the probability of success of specific treatments are displayed on a graphical user interface. The system searches for patterns in the patient data and profile lists that reflect those specific risks and success probabilities. A high probability of disease risk or of the success of a specific treatment is indicated on the graphical user interface.

24 Claims, 10 Drawing Sheets

Image Based Patient Profile

- Aortic calcification     0.5ml
- Average spine disk thickness     2mm
  - L5 5.1mm
  - L4 1.2mm
  - L3 3.2mm
  - ...
- Total number of lymph nodes >10mm     7
  - Paraaortic 7
  - Iliac 0
  - Inguinal 0
  - Abdominal 0
  - Axillary 0
  - mediastinal 0
- Total Volume of lymph nodes     32ml
  - Paraaortic 5ml
  - Iliac 0ml
  - Inguinal 0ml
  - Abdominal 0ml
  - Axillary 0ml
  - mediastinal 0ml
- "Weight" of lymph nodes     2910 ml*HFU
- Volume Liver     2400ml
- Volume Heart     744ml

FIG. 3

META PATIENT PROFILE 18

| IMAGE MODALITY PRIMARY CATEGORY | IMAGE MODALITY SECONDARY CATEGORY | IMAGE-BASED MEASUREMENT TYPE | MEASURED VALUE | DEVIATION OF MEASURED VALUE FROM NORMAL RANGE |
|---|---|---|---|---|
| MICROSCOPY | H&E | NUMBER OF MITOSES PER 1000 CELLS | 5 | ⇧ |
| | | RELATIVE NUCLEUS SIZE OF TUMOR CELLS | +30% | ⇧ |
| | IHC/ER | PROLIFERATION INDEX | 10% | ⇩ |
| COMPUTER TOMOGRAPHY | | NUMBER OF ENLARGED LYMPH NODES | 3 | ⇦ |
| | | TOTAL VOLUME OF THE LARGEST LYMPH NODES | 130 mm³ | ⇦ |
| LABORATORY VALUES | BLOOD | ERYTHROCYTES | 5 Mio/ul | ⇧ |
| | | LEUKOCYTES | 400 Mio/ul | ⇩ |
| | | BILIRUBIN | 1.1 mg/dl | ⇧ |
| | URINE | pH value | 5.5 | ⇧ |

ALTERNATIVE REPRESENTATION

| DEVIATION OF MEASURED VALUE FROM NORMAL RANGE |
|---|
| 5 |
| +30% |
| 10% |
| 3 |
| 130 mm³ |
| 5 Mio/ul |
| 400 Mio/ul |
| 1.1 mg/dl |
| 5.5 |

FIG. 7

IMAGE-BASED PATIENT PROFILES

TECHNICAL FIELD

The present invention relates generally to generating image-based patient profiles with a list of measured values and indications for abnormalities of those values that are outside of a given norm, and more specifically to a system for computer-aided diagnosis that links those patient profiles to regions in the digital images that relate to the corresponding abnormal measured values.

BACKGROUND

Systems for detecting and analyzing target patterns in digital imagery have a wide variety of uses. An increasingly important area is the detection and analysis of anatomical regions in the human body. For example, radiological images from computed tomography (CT) are used for the computer-aided detection (CAD) of various ailments in human organs. Images from magnetic resonance imaging (MRI) are also used in computer-aided detection. The large amount of information generated by computer-aided detection systems is difficult for pathologists and radiologists to assimilate. Pathologists and radiologists currently base their diagnoses only on a small portion of the overall information that they choose based on subjective criteria.

An improved CAD scheme is sought that identifies the most important information obtained from the analyzed digital images and guides the user to the source of that information.

SUMMARY

A system assists a user to perform computer-aided detection by generating image-based patient profiles. The system acquires digital images from tissue samples and CT and MRI scans. The system detects objects within the images. The system measures values related to the detected objects and displays the measured values in lists. The lists and images together form an image-based patient profile. The patient profile indicates the normal ranges for measured values. The system indicates which measured values fall outside the normal ranges. The system navigates the user to the objects in the images that are associated with the abnormal values when the user selects a measured value in the patient profile.

The system includes a patient database, a data analysis server and a graphical user interface. A digital image is stored in the database. For example, the digital image is acquired by an optical microscope from a tissue sample or by a computer tomography device. The digital image can be a time series of digital images. The data analysis server recognizes a group of objects in the digital image and measures a value associated with the recognized group of objects. The data analysis server then evaluates the measured value as critical because the value falls outside of a normal value range. The data analysis server stores the measured value in the database and displays the digital image, the measured value and the normal value range on the graphical user interface. The normal value range is displayed on the graphical user interface as a histogram. The age and the sex of a patient are stored in the patient database, and the data analysis server determines the normal value range based on the age and the sex of the patient.

In one embodiment, the system displays a portion of the digital image that contains the group of recognized objects on the graphical user interface. The system displays the measured value within a context of other values in a predetermined group of values. The user selects from a selection box on the graphical user interface between different contexts leading to different normal ranges. The system navigates the user to objects of the group of recognized objects in the image when the user selects a field on the graphical user interface that is associated with the measured value.

One context within which the measured value is displayed on the graphical user interface is represented by the change of a value from one time step to the next. Other contexts are represented by an assumed treatment of the patient, an assumed medication for the patient, or an assumed disease.

The system displays different patient profiles, including image-based patient profiles, side-by-side in a unified form as a comprehensive patient profile, which is called a Meta-Patient Profile (MPP). In another embodiment, an additional type of patient profile is added to the MPP, called the Super-MPP. A Super-MPP illustrates how a potential pattern, such as a disease pattern or treatment recommendation pattern, for the comprehensive patient profile is predefined, and how a match between the values in the comprehensive patient profile and the predefined pattern is measured. The result of the matching is presented in the Super-MPP on the graphical user interface.

There are two different components incorporated into the Super-MPP. One component is disease related and the other is treatment related. Both kinds of Super-MPP are meant to help the attending physician arrive at the correct conclusion with respect to the diagnosis on the one hand and with respect to the correct treatment on the other hand. In the disease-related Super-MPP (Super-MPP-d), different measured values in the MPP are taken to calculate a new value that represents a measure of the probability of the patient being healthy with respect to a specific disease. In this manner, the strength of certain disease patterns is tested. For different types of diseases, such values are displayed in the Super-MPP-d. Whether such a value falls inside or outside the normal range of healthiness is indicated on the graphical user interface.

In the treatment-related Super-MPP (the Super-MPP-t), different measured values in the MPP are taken to calculate a new value that represents a measure of the probability of the patient being responsive in a positive sense to a specific treatment. In this manner, the strength of certain responsiveness patterns with respect to specific treatments is tested. For different types of treatments, such values are displayed in the Super-MPP-t. Whether such a value falls inside or outside the normal range of positive responsiveness is indicated on the graphical user interface.

The system detects a disease or treatment pattern for the entirety of all patient profiles of one patient, and the values of the profiles that contributed to the disease or treatment pattern, i.e., to the calculated value in the Super-MPP, are highlighted in the MPP when the user selects the calculated value in the Super-MPP.

A method of computer-aided diagnosis involves indicating which measured oncological or pathological values of a patient fall outside their normal ranges by analyzing digital images of the patient. The method includes analyzing a digital image, detecting a group of objects in the image, and measuring a value related to the group of objects in the image. The measured value is then displayed in a patient-profile list that indicates that the measured value falls outside the normal range. The normal range of the measured value is displayed as a histogram on a graphical user interface. When the user of the system selects an area on the graphical user interface that is associated with the measured value that falls outside the normal range, the user is navigated to a section of the image containing objects from the group of objects.

The size of the section of the image is configurable using a graphical user interface element. The group of objects can be displayed as an object detection result overlay. A three-dimensional digital image can be displayed as a two-dimensional cross section or as a three-dimensional projection depending on settings defined using a graphical user interface element.

The group of objects are typically anatomical objects of the patient. Various values can be measured, such as the average volume of the anatomical objects, the number of objects within the group of objects, or the average surface area of anatomical objects. The patient-profile list can also include blood values of the patient.

In another embodiment, a second value related to a second group of objects in the digital image is measured. The system indicates that the second measured value falls outside a second normal range. If the second measured value falls farther outside the second normal range than the first measured value is outside of the first normal range, then the system navigates the user to the second group of objects before navigating the user to the first group of objects. In one aspect, the image section is displayed to the user that is related to the objects having the largest difference in measured values with respect to the normal range. In another aspect, the second group of objects belong to a different health state than do the first group of objects. For example, the second group of objects belong to a different cancer type than do the first group of objects.

In another embodiment, a second digital image is analyzed that depicts anatomical objects at a point in time after the anatomical objects in the digital image were acquired. The value associated with the anatomical objects in the second digital image is also measured and compared to the value measured from the first digital image. The comparison of the value measured from the second digital image with the value measured from the digital image is displayed on the graphical user interface.

In another aspect of the method, different digital images are analyzed, and groups of objects are detected in the images. Values related to the groups of objects in the images are measured. The system defines a potential pattern within the numerous measured values related to a particular disease and calculates the strength of a fit of the measured values to the potential pattern. The system indicates on a display that the measured values fit the potential pattern.

In another embodiment, a method includes measuring at least two different types of values listed in a meta-patient-profile and then calculating a new value from the measured values. The new value is a measure of the probability that the patient has a specific disease. The new value is displayed in a super-meta patient profile (SMPP). The SMPP indicates that the new value falls outside the normal range for healthy patients.

In yet another embodiment, a method includes measuring at least two different types of values listed in a meta-patient-profile and then calculating a new value from the measured values. The new value is a measure of the probability that the patient will positively respond to a specific treatment. The new value is displayed in a super-meta patient profile (SMPP). The SMPP indicates that the new value falls outside the normal range of positive responsiveness.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 3 is an example of an image-based patient profile generated from a CT scan.

FIG. 7 shows an exemplary image-based patient profile.

DETAILED DESCRIPTION

Reference will now be made in detail to some embodiments of the invention, examples of which are illustrated in the accompanying drawings.

Figure 1:
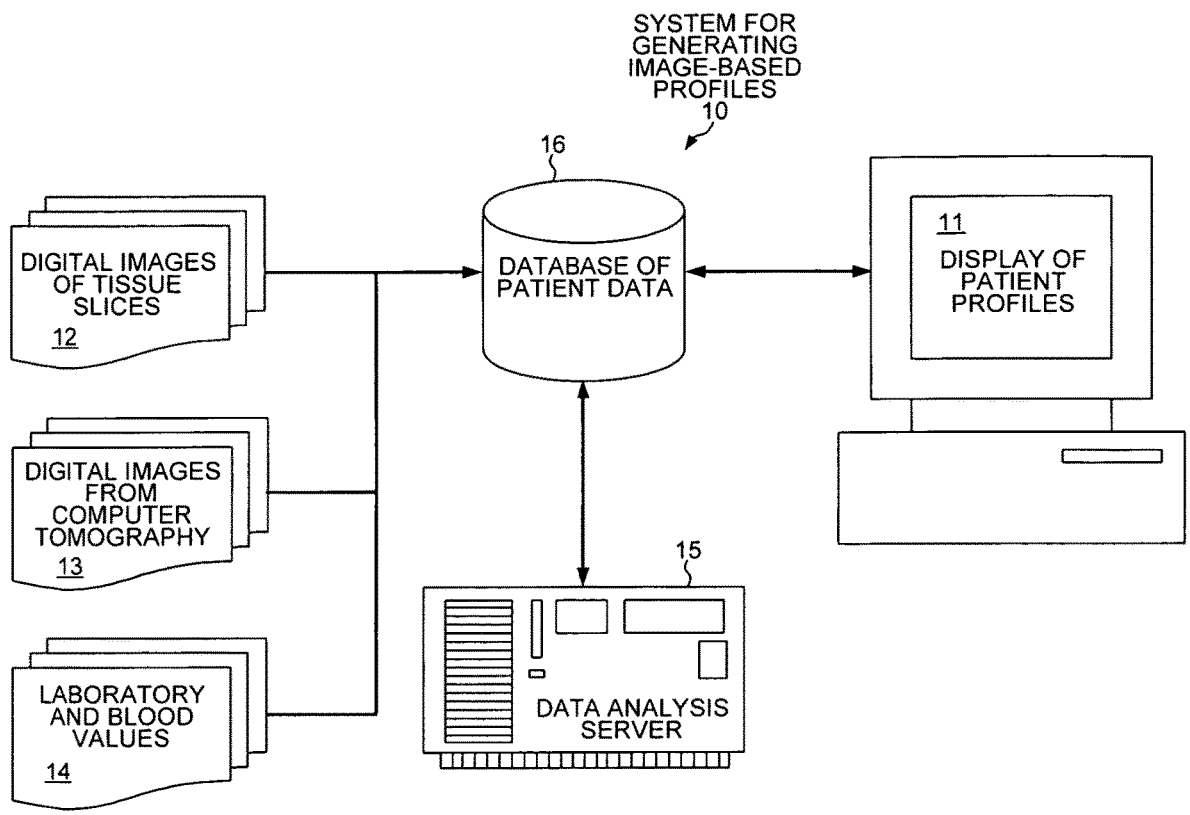
FIG. 1 is a diagram of a system for generating image-base patient profiles.

FIG. 1 shows a system 10 for generating image-based patient profiles. The effectiveness of medical treatments can be improved and the cost of those treatments can be reduced by performing complex image-based measurements on medical patients. The image-based measurements obtained from automated, intelligent image analysis are used to generate image-based patient profiles, which can improve the quality of everyday clinical practices. The patient profiles include lists of values for the parameters that are measured by analyzing medical images. The patient profiles also include evaluations of the individual measured values. Individual measured values that are evaluated to be critical are linked to the associated image regions on a graphical user interface 11.

The patient profiles enable radiologists and pathologists to arrive at diagnoses significantly faster and to base those diagnoses upon objective numbers. In addition, treating physicians can combine different types of patient profiles, such as blood counts, blood test results, and general patient data, to form a comprehensive clinical overview. The patient profiles become the basis for communication among the pathologists, radiologists, treating physicians and patients.

In addition to improving medical diagnosis, the image-based patient profiles also allow other factors to be considered. For example, the side-effects that occur during a drug treatment can be identified and graphically displayed to the treating physician.

The medical images that are analyzed to generate the patient profiles must be acquired in or converted to digital form. The medical images may be three-dimensional or multidimensional image data sets. The images may also be composites of multiple image data sets acquired from different imaging processes, or the same imaging processes at different time steps. For example, an image may be acquired using positron emission tomography combined with computer tomography (referred to as PET-CT). Image-based patient profiles can form the basis for proper treatment of a patient rather than the rough subjective inspection of medical images that is currently being performed.

FIG. 1 shows three sources of digital images used to generate image-based patient profiles. For example, the digital images can be obtained from tissue slices 12 in pathology, from computer tomography scans 13 in radiology, and from laboratory work on blood samples 14. Additional input data includes patient demographic data and ultrasound data that is formed into a patient profile or is used as context information for calculating the range of uncritical values. For example, the size of organs depends on the age of the person, and the uncritical range for those sizes can be calculated by using the age of the patient as context information.

The image-based profiles are generated using intelligent image processing and automated classification and quantification. System 10 performs the classification, quantification and evaluation using a data analysis server 15. For instance, an image-based profile is generated for a patient's image of an H&E-stained tissue sample acquired using light microscopy. The profile lists the properties and associated values of objects contained in the patient's image. Relevant object classes are tubulus, gland, vessel, epithelium, stroma, cell, nucleus, cytoplasm, membrane, micronucleus, chromatin, reticulum. The image-based patient profile is generated using statistical values from different kinds of object groups. Each object group is defined by the classification of the objects in combination with additional conditions. For example, the average size of all nuclei is calculated, as well as the average size of all cancer nuclei or of all cancer nuclei fulfilling a certain condition, e.g., with respect to their color or shape. The image profile is numerically based and can thus be generated with a high degree of automation. Creating a complex list of properties with the corresponding values manually would be prohibitively expensive. In addition to properties of the image of H&E-stained tissue, images stained by immunohistochemistry are also evaluated. Physicians currently evaluate microscopic images using qualitative or semi-quantitative scoring methods. But there is currently no numerical basis for objective judging the tissue state based on an image.

The system for generating image-based patient profiles provides highly relevant clinical information that cannot be obtained through conventional image classification. Image-based patient profiles could become an indispensable basis for a doctor's decisions in the same way that blood count levels are currently relied upon. Diverse properties can be measured. One exemplary property is a statistical analysis of the sizes of various types of objects, such as the size of cell nuclei (used in pathology) or the size of lymph nodes (used in radiology). Currently, the sizes of objects are not comprehensively collected, but rather are collected on the basis of a few selected samples. In practical terms, the comprehensive measurement of objects in a CT scan or in a scan of a tissue sample cannot be performed manually. Currently, only isolated, selected sample measurements are possible, which are unsuitable for presentation in the form of a patient profile. Measured values of properties of the simplest image objects are not currently available for use in evaluating patients.

In the field of radiology, system 10 for generating image-based patient profiles provides morphological data on a wide range of anatomical objects. The intensity of each image object, as well as its brightness pattern, is displayed. In the field of pathology, intensity, brightness and color patterns are analyzed at a molecular level using stains, biomarkers, antibodies and contrast media. This molecular analysis is even more valuable than the non-localized molecular analysis of blood tests because the location of the analyzed tissue is also provided. Through image analysis, system 10 determines not only the concentration of the particular molecule being analyzed, but also the location of the molecule in the body (for radiology) or the location in the cell matrix (for pathology).

Thus, system 10 can be used for both radiology and pathology. Historically, image analysis in radiology was performed on digital images, whereas digital image analysis was not performed for pathology. The digitization of images began much earlier in the field of radiology, driven by imaging techniques such as MRI and CT, which are digital in nature. However, digital images used in pathology are becoming more common, and patient profiles that integrate the two fields will become available. These new comprehensive image-based profiles will enable new types of diagnoses and treatments. Important information will be revealed that would otherwise have been inaccessible.

I. Implementation of the System in the Field of Pathology.

System 10 for generating image-based patient profiles is used for computer-aided pathology (CAP). CAP is a special form of computer aided diagnosis (CAD). For pathology, system 10 generates tissue-based patient profiles (TPPs). Images of a tissue sample must be provided in digital form. The digital images are generated using a tissue section scanner with a data volume of approximately 1 GB per digital image of a tissue section.

The tissue-based patient profiles (TPPs) include a plurality of measured values as well as the evaluation of these measured values. The tissue-based patient profiles (TPPs) are stored in a database of patient profiles 16. The measured values and the evaluations are then linked to the associated image objects. In most cases, the measured values are statistical values resulting from measurements of a large number of similar objects. Examples of such values include the number of all detected cell nuclei, their average size and their average color tone. Ordinarily, however, the objects to be examined are analyzed and measured in highly differentiated fashion. For instance, it is not sufficient to treat all nuclei alike. The cell nuclei must at least be classified as healthy or unhealthy nuclei. For oncological examinations, tumor regions must be identified, and the statistical measurements in these regions must be treated separately from those in healthy tissue areas. It may also be necessary to further differentiate the tumor regions. Because tumor cells undergo new mutations over the course of further cell divisions, and the gene repair mechanisms in tumor cells no longer function properly, the variety of tumor types in a person afflicted with cancer increases over time. This variety must then also be reflected in the TPP. At a somewhat earlier stage, however, it may also be possible to differentiate different types of tumors. Separate TPPs are generated for each type of tumor, as well as for the healthy tissue. A TPP is organized hierarchically and divided into classified regions. Each tissue class has its own sub-TPP with potentially very similar parameters, but different measured values. The separate TPPs are generated not only for oncological examinations but also for other types of evaluations, such as for inflamed areas or those with signs of wear.

Computer-aided pathology provides at least three benefits. First, the TPPs quantify the analyzed parameters, and the quantification allows an objectification of the evaluation. Second, the problem of finding the "needle in the haystack" is solved or at least drastically reduced. Third, complex tissue profiles allow for a better diagnosis than tissue classifications or evaluations with mostly only one (a grading value) or in some cases only a few values being presented.

A. Quantification.

Manual quantification of analyzed parameters is far too time-consuming and is unfeasible and cost-prohibitive in everyday practice. In order to evaluate the analyzed parameters, pathologists currently spend a great deal of time very carefully and intensively examining different areas of the tissue section in the medical image. In addition to subjective evaluation, quantitative methods are increasingly playing a role in classic pathology. For example, pathologists currently must manually count the number of positive (darkly colored) and negative (lightly colored) tumor cells in a viewing field of a microscope. Most pathologists have the necessary knowledge and a wealth of experience, and are able accurately to evaluate the tissue structures and the degree of coloration. Such current evaluations, however, have been proven to be subjective and dependent upon mood. System 10 for generating image-based patient profiles provides the pathologist with concrete numbers that enable the pathologist to draw conclusions faster and more objectively. The pathologist can then concentrate on random samples presented by the system as decisively related to the critical values for verifying the automatic measurements generated by system 10.

The pathologist uses the tissue-based patient profiles (TPPs) to navigate to these random samples in an intelligent manner. System 10 navigates to the regions of the image in which these values from the TPPs were obtained, and these regions are displayed to the user on a monitor. System 10 allows the user to sort these regions by criteria, and the user can "page through" from the first section of this sorting list to the last in a type of image viewing. The user can skip to the next measured value at any time when he has seen enough, and can click on a field there to start the next image viewing. Because the measured values are evaluated, the user can concentrate on the critical measured values for the random samples. These critical measured values are measured values that have been evaluated as poor, meaning that such a measured value is either too high or too low as compared with average values of the same type for normal tissue.

With automatic quantification, pathologists can make decisions faster and with a better basis. The pathologist is also guided to specific relevant regions based upon the quantified numbers. The quantification reduces costs both by allowing the pathologist to work more efficiently and by preventing incorrect diagnoses and the resulting improper treatments.

B. Needle in the Haystack Problem.

Tissue samples represent huge quantities of data that cannot be viewed comprehensively by a pathologist. Consequently, the pathologist is confronted with the "needle in the haystack" problem.

The pathologist currently scans the cell sample at a low microscopic resolution and then examines only those areas at high resolution that look interesting to him at the lower resolution. This method necessarily overlooks important data and leads to errors in diagnosis. If a pathologist were to search the entire tissue section manually at high resolution, it would take much too long, and the result would still be inadequate. Many studies on this topic exist, all of which show that humans have great difficulty with systematically searching large areas. Machines have no difficulty searching large areas; they do not lose patience, they do not become bored, they do not become distracted, and they examine each individual pixel within its own context. For example, system 10 is especially adapted for counting mitotic cells in an haematoxylin and eosin (H&E) stained cell sample. The resulting number is one of the basic parameters used for tumor evaluation based upon the mitotic index.

C. Values Lists in Tissue-Based Patient Profiles.

Because a manual quantification of tissue sections is possible only with extreme limitations, pathologists are currently limited to simple classification. The pathologist currently evaluates each tissue section as good, bad or undefined. In the third case, another examination is performed. Automated image analysis allows evaluations to be performed that go beyond simple classification. While system 10 performs the customary classification, system 10 also generates tissue profiles that include lists of tissue section values. Tissue-based patient profiles (TPPs) include lists comparable to those generated for blood analysis. While blood count levels represent mostly non-localized chemical and biological information, the tissue values in TPPs represent molecular information for which the location is also known. Thus, using the staining methods of immunohistochemistry (IHC) and in situ hybridization (ISH), not only is the concentration of certain molecules (such as proteins, RNA, DNA, genes) in a cell known, but also precisely where these molecules are found within a cell, in what cell, and in what cell system. In other words, this is high-value information that cannot be derived by molecular diagnostics. System 10 measures a multitude of objects and structures within the tissue sample and creates a tissue profile in the form of a values list.

Using TPPs improves diagnoses. For example, the life expectancy of patients with stomach cancer can be predicted with high statistical accuracy using the values lists of tissue profiles. A diagnosis based on a tissue profile is more accurate than a diagnosis based only on a tissue classification.

FIG. 2 shows a life-expectancy diagnosis of a particular patient with gastric cancer based upon a regression model that correlates the measured parameters of a tissue section from the patient to the known survival times of many patients in the past. The measured parameter is a Her2-based brown staining of the cytoplasm of tumor cells in proportion to the brown staining of the cell membrane. Patients were classified into "long-lived" and "short-lived" groups based on a threshold of forty-six months on the scale "disease free survival time." The image analysis software of system 10 generated TPPs with not only more informational content than current classification data, but also having more complex information. Thus, generating the TPPS is only a first step in determining the diagnosis. In later steps, system 10 evaluates each value in the lists of values in the tissue-based patient profiles.

Figure 2A:
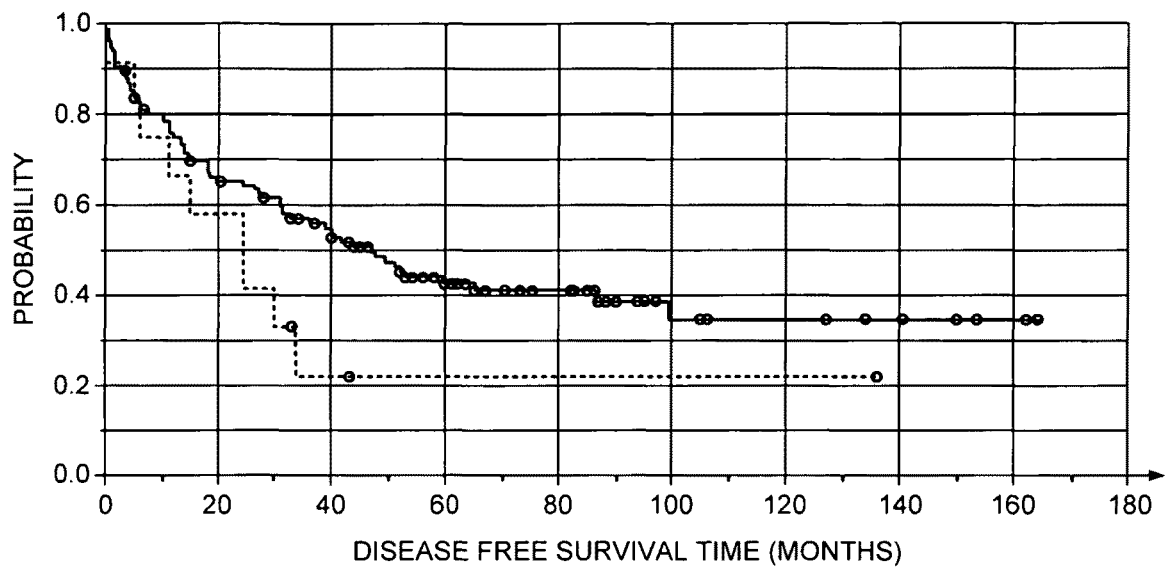
FIG. 2A is a chart showing a life-expectancy study of cancer patients based on the manual classification of a tissue section from the patient.
Figure 2B:
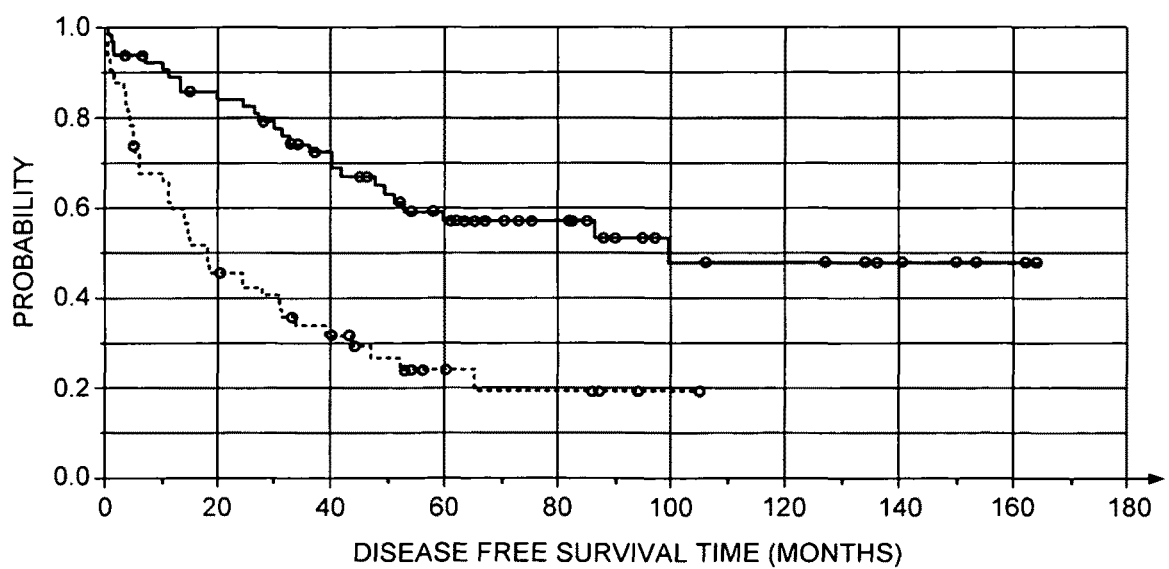
FIG. 2B is a chart showing a life-expectancy study of cancer patients based on the analysis of the tissue section from the patient performed by the system of FIG. 1.

FIG. 2A shows the life-expectancy diagnosis based on a manual classification performed by the pathologist, whereas FIG. 2B shows the diagnosis based on the evaluated measured values obtained from system 10. The higher curve in each figure represents a non-malignant form of tumor cells in the patient's cytoplasms, whereas the lower curve in each figure represents malignant tumor cells. The survival time for patients on the lower curve is much shorter. Using manual classification in FIG. 2A, the survival times of the two groups of patients does not significantly differ statistically ($p<0.1137$). The image analysis performed by system 10 that generates the diagnosis in FIG. 2B, on The other hand, with survival times for the two groups of patients that differ significantly ($p<0.0001$).

The curves in FIG. 2 compare the prognostic value of a visually assessed scoring algorithm derived from Dako HercepTest™ with results from quantitative image analysis generated by system 10. The results were obtained using three tissue microarrays (TMAs) comprising 391 cores from tissue samples from 150 patients. After IHC staining with Her2 antibody the TMAs were scanned with Zeiss MIRAX slide scanner (20× objective). System 10 segmented and classified cells, nuclei, cytoplasm and membrane objects, and determined on a per cell basis shape, texture and color properties. These properties were correlated with known disease-free and overall survival times using a multivariate regression analysis. Based on this predictive model, the patient population was divided in one group with good and one with poor prognoses by imposing a threshold on the predicted survival times. The corresponding groups obtained by the pathologist scoring were Her2 score 0, 1+, 2+ versus Her2 score 3+. The Kaplan-Meier analysis performed by system 10 revealed a significant (DFS: $p<2.4\times10-6$; OS: $p<2.5\times10-7$) prognostic value for the two groups, whereas the visually assessed score was not significant ($p>0.1$).

II. Implementation of the System in the Field of Radiology.

Currently, there are only a small number of evaluation tasks in computer-aided diagnosis (CAD) that a machine can perform robustly. Moreover, higher quality diagnoses are currently demanded by patients from radiologists than are demanded from pathologists because radiological diagnoses frequently relate not only to statistical information but also to specific anatomical objects. In the pathology field, overlooking a particular cell does not create a problem because there are plenty of other cells with the same characteristics. On the other hand, in radiology the factor of three-dimensionality is added, where machines have less difficulties than do humans. Three-dimensional radiological scans, such as CT or MRI, are not easily processed by humans, as humans do not have three-dimensional eyes. The current standard method of scrolling through images is an imprecise method of obtaining an impression of a three-dimensional radiological scan section. In the future, perhaps also three-dimensional microscopic methods that already exist today will become standard techniques and a demand is also created for 3D image analysis in pathology. In radiology, three-dimensional images are already standard today, and in cardiovascular applications three-dimensional visualization methods exist. In general in areas where the contrast is high by nature (in CT: bones or lesions in lung) or can be elevated by contrast enhancing procedures (contrast bolus in blood vessels or stomach or intestine or gas in intestine) three-dimensional visualizations are common practice. In most fields of oncology, however, there are currently no three-dimensional visualization methods as the contrast levels are too weak and contrast enhancing procedures do not exist or are very expensive and have side-effects because of the required radioactive radiation (PET).

System 10 for generating image-based patient profiles solves the problem of evaluating a three-dimensional radiological scan section by enabling a semantic visualization of the section. In semantic visualization, in addition to the contrast, texture and brightness of the objects, the context of the objects is used to detect the objects. Therefore, semantic visualization can be used to evaluate low contrast three-dimensional objects in radiological scans.

Computer-aided diagnosis in the field of radiology offers several benefits. First, the quantification allows an objectification of the evaluation. Second, the problem of finding the "needle in the haystack" is solved. Third, tissue-based patient profiles provide a better diagnosis than simple tissue classification. Fourth, semantically detected and visualized objects (especially with three-dimensional images) linked to the corresponding measured values of the profile improves and accelerates evaluation.

A. Quantification.

In current radiological practice, no true quantification is performed in the field of low contrast oncology, which represents the majority of oncological problems in radiology. Rough two dimensional estimated values, such as RECIST, are available as a stopgap measure to the lack of three-dimensional access to the data by humans. Because many clinical decisions are dependent upon quantifications that are currently replaced with estimates, a method of quantification is long overdue. This need for precisely quantifying individual objects is not as urgent and widespread in pathology.

Currently, three-dimensional radiological measurements are unobtainable in a reasonable time period. System 10 now provides automatic three-dimensional measurements and quantification. In addition, the tissue-based patient profiles provide significantly more information from the medical images. Not only are those anatomical objects that are the focus of interest measured, but comprehensive measurements are also performed. For example, using CT or MRI images, system 10 can measure the volume of the liver, heart and other anatomic objects of a patient with intestinal cancer, which otherwise could not be done due to time constraints. System 10 presents the radiologist with this additional information upon which new methods of diagnosis can be based. During clinical monitoring of a cancer treatment, for example, the physician is notified of undesirable side effects of the treatment as a result of the automatic detection of unusual changes in the texture, density, shape and size of anatomical organs. Within the context of staging in radiology, in addition to the measured values themselves, the change in the values over time is evaluated in the image-based patient profiles.

B. Needle in the Haystack Problem.

Three-dimensional scans represent large quantities of data that the radiologist cannot view comprehensively. Thus, the radiologist is confronted with the "needle in the haystack" problem. Consequently, radiologists currently view only those areas of a medical image in which the radiologist expects to find something of interest. In this process, essential errors necessarily occur, and significant findings are overlooked. If the radiologist were to carefully search the entire scan, it would take much too long, and the result would still be inadequate. Many studies on this subject exist, all of which show that humans have great difficulty systematically searching large image areas. Humans rapidly become bored, and can be distracted. If a human finds something remarkable in one area, all of his attention is drawn there, and he overlooks findings in neighboring areas. System 10 for generating image-based patient profiles, however, does not lose patience, does not become bored, does not become distracted, and examines each individual pixel within its own context. The image-based patient profile guides the radiologist specifically to those objects that the radiologist has overlooked. (Image-based patient profiles IPPs) in the field of radiology as opposed to pathology with the tissue-based patient profiles (TPPs) are here called scan-based patient profiles (SPP).)

C. Radiological Patient Profiles.

Image-based patient profiles provide a better diagnosis than simple scan classification. True quantification is currently not performed. And even rough approximation methods, such as RECIST, are currently performed only in exceptional cases. The majority of anatomical objects are not currently quantified in any way. Innumerable anatomical objects are included in a CT scan, for example. All of these anatomical objects can be measured by system 10.

Each human body is built differently, just like every person has different blood count values. Value ranges can be defined within which the respective concrete values can be evaluated as "normal." This applies to blood count values just as it applies to anatomical characteristics. Although blood count values are currently measured, anatomical characteristics are not.

System 10 for generating image-based patient profiles performs intelligent image processing in radiology and thereby evaluates the characteristics of organs and other anatomical objects. Although the relevance of some measurements of organs is apparent today, the relevance of many organ measurements will be discovered only in coming years. The experience as to what is normal and what is not has also to be developed over time. New marking and contrast intensification methods will also be developed that will enable entirely new measurements.

Some organ measurements for which the medical relevance is currently obvious are: the thickness of each individual intervertebral disk (e.g., L5 is 5 mm), the maximum spinal curvature, the organ volume (e.g., of the heart), the total volume of all lymph nodes above a threshold size, the total volume of all mediastinal, inguinal or other type of lymph nodes, the individual density of the five largest lymph nodes, the total volume of aortic calcification, the relative liver volume with 25% below-average blood flow, and the relative blood flow in the liver, spleen, or kidneys (measured as the intensity of blood contrast medium).

In addition to measuring absolute values, system 10 measures changes in the values of measurements at different times. System 10 then displays the changes in the values of the IPP. The measured values as well as the change in the values are evaluated. For example, the measured values for an anatomical object of a patient are compared to the values obtained in a follow-up examination. The change in the values is an indicator of the side effects of medications on the evaluated organ. The list of relevant scan values can be very long. The list does not become unwieldy, however, because system 10 notifies the treating physician of those measured values that are evaluated as being abnormal.

D. Semantic Visualization.

Wherever a robust 3D visualization is possible and necessary, it is used today in clinics. The value of a 3D display is recognized, but it is not necessary in simple cases. Consequently, 3D visualization is used when it functions robustly and in order to handle a complex problem. Thus, 3D visualization is used today in the following narrow range of fields: complex vascular investigations, complex bone fractures and virtual intestinal analysis. CT scans provide high contrast images of bones (by nature) and blood vessels (with contrast bolus), and the contrast of images of the intestines can be artificially enhanced using contrast media such as gases. In oncology, there are no high-quality 3D visualizations today because typically there is insufficient contrast in MR and CT scans of lesions and lymph nodes. Although PET scans offer good contrast, they provide a poor 3D resolution and are very expensive and time intensive.

System 10 links the measured values to the measured objects in the medical image through semantic visualization. For example, system 10 links measured values to objects in a three-dimensional image of an intestinal endoscopy, a complicated bone fracture or a complex vascular examination. Bones are very high-contrast in CT scans, and both blood vessels and the intestine can be made artificially high-contrast using contrast media (gases for the intestine). Besides investigations of the intestine, other situations in oncology are more complicated. In one case in oncology, i.e., for detection of lesions in the lung, the contrast is high by nature for CT scans, as air has a much lower density than all kinds of tissue. All other cases in oncology could be called "low-contrast cases". In low contrast oncology, no products that generate three-dimensional visualizations currently exist in the market because lesions and lymph nodes in MRI and CT scans are generally very low-contrast. Although PET scans display good contrast, they possess poor spatial resolution. On the other hand, semantic segmentation changes this situation as demonstrated in FIG. 4, where low contrast organs are also detected.

Semantic segmentation and visualization offers a solution for oncology. Using intelligent image processing, even low-contrast objects can be represented in very beautiful three-dimensional representations. The low-contrast objects are detected in a manner that is driven by context and knowledge, i.e., semantically, and can then be represented three-dimensionally. In this case, the surface of the measured objects is represented three-dimensionally. Since these surfaces can also be represented in a semi-transparent way, even objects that are within a covering object are made visible to the user (for example, tumors in a liver). Each measured object (at any scale) can be changed to visible or invisible by an input from a user.

In this manner, both anatomical objects acquired at high contract and those acquired at low contrast can be depicted to the user in a single semantic visualization. The physician thereby gains an overview of evaluated values for multiple organs. System 10 documents all remarkable features in each scan evaluation, including those that are not the focus of the examination in question. Although the evaluation of the entire MRI or CT scan is a very complex task, the overall complexity of the evaluated values is drastically reduced by the three-dimensional visualization. The intelligent image analysis provides the opportunity to use three-dimensional visualization on a very broad basis for large enough scan ranges with enough context objects being available (e.g., more than 25% of the patient's torso).

In the three-dimensional visualization of the anatomical objects in a medical scan, the visualization of the image-based patient profile can also be used. The anatomical objects whose listed value falls outside the normal range can be enhanced via color values, or spatial or temporal patterns. By linking the evaluated measured values of the IPP with the regions in which these measured values were obtained, the physician can be guided conveniently by clicking on his monitor on a field provided for that purpose. For example, by clicking on a measured value, the visualization centers on the measured anatomical region. The image details of this region are then simultaneously presented to the physician. Two-dimensional, three-dimensional and semantic visualizations are displayed to the physician, which makes the segmentation of the objects and their classification visible (for example, by color coding).

FIG. 3 shows an example of an image-based patient profile (IPP) generated from a CT scan. Those measured values that are outside of the normal limits, are emphasized with cross-hatching. The TPP indicates the evaluations of seven measured values: the calcification of the aorta, the thickness of various intervertebral disks, the number of various types of lymph nodes that are larger than 10 mm, the total volume of the lymph nodes of each type, the total intensity of the lymph nodes objects in the scan, the volume of the liver and the volume of the heart.

Figure 4:
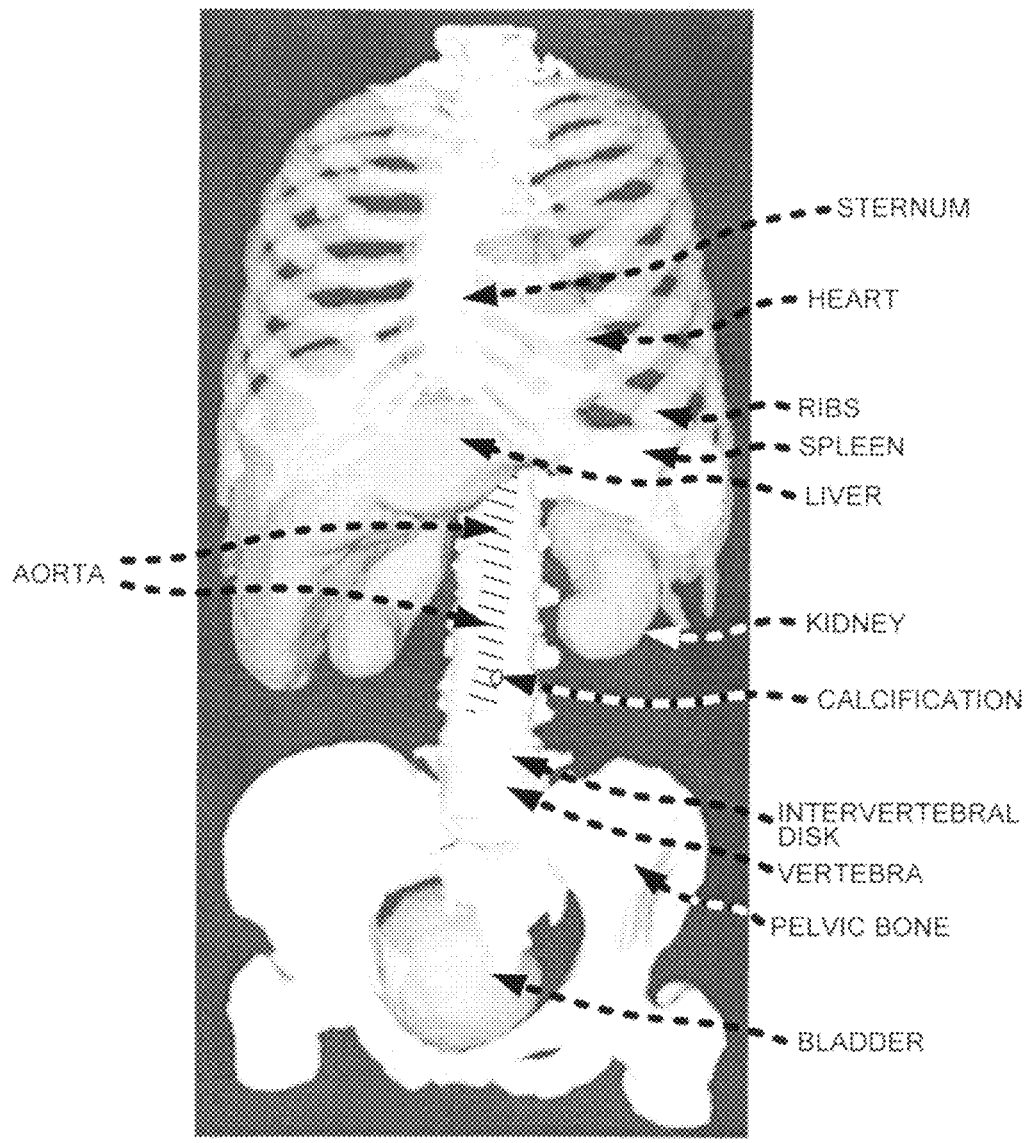
FIG. 4 shows a three-dimensional semantic visualization of anatomical objects in a CT scan generated by the system of FIG. 1.

FIG. 4 shows a three-dimensional semantic visualization of anatomical objects in a CT scan generated by system 10 for generating image-based patient profiles. The objects have been measured, and a calcification on the aorta has been identified for the physician. The aorta is marked with cross-hatching because a measured value of the aorta (the calcification) is outside the normal limits. When the user clicks on a field in the IPP that is assigned to the abnormal value for aortic calcification, a section of the scan containing the object with the measured value outside of normal limits is presented.

Figure 5A:
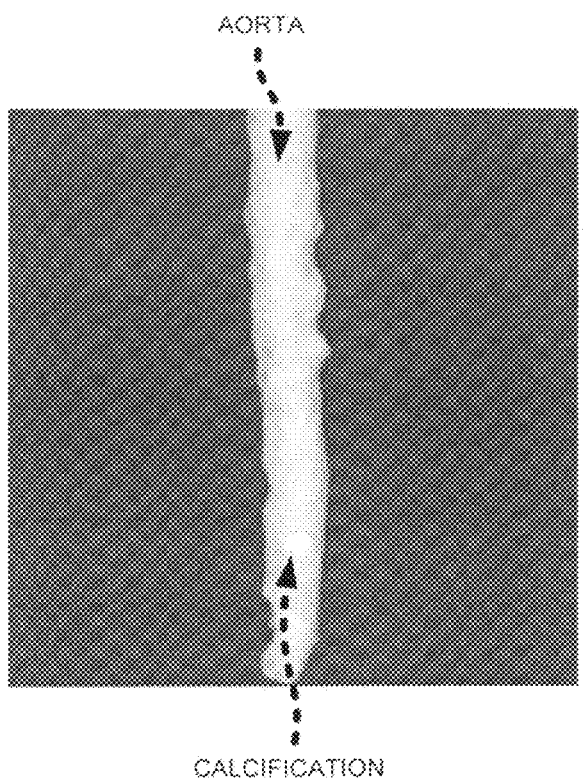
FIG. 5A is a three-dimensional semantic visualization of an object related to an abnormal measured value.
Figure 5B:
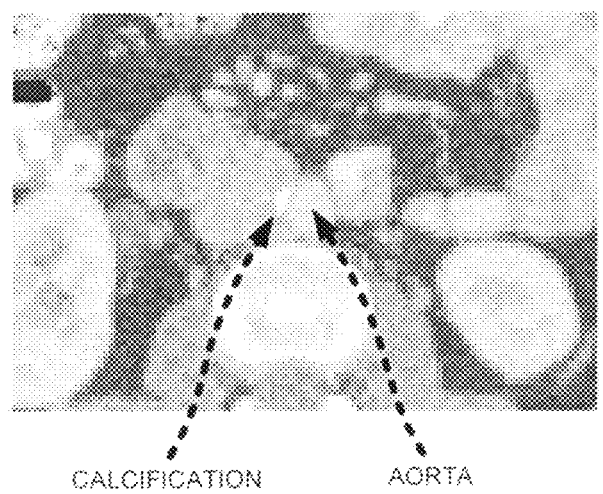
FIG. 5B is a two-dimensional semantic visualization of the object of FIG. 5A.

FIG. 5A shows a three-dimensional semantic visualization of the objects related to the abnormal measured value. The visualization shows a gray aorta with a bright region of calcification. The user is also presented with a two-dimensional cross section of the area of interest with the bright calcification in the center. FIG. 5B shows the two-dimensional cross section of the area of interest.

The image analysis system is able to evaluate a plurality of measured values. The method for evaluating these values enables a physician to make high-quality medical diagnoses because of the following advantages over the current evaluation methods.

1. The system does not rely on only a few randomly sampled and subjective values. Three-dimensional CT or MRI scans as well as tissue samples for biopsies represent a huge amount of information. It would be prohibitively expensive and time consuming to measure the multiple objects manually. An evaluation of a tissue section or a CT scan is currently limited to a few object types; and even among those only a few are measured as random samples. The selection of random samples is currently left to the pathologist or the radiologist, and is thus highly subjective. Moreover, in the case of tissue sections, it is in most cases not possible to determine at a later time from where these random samples were collected. Very simple images with a content of low complexity can be measured manually. However, the evaluation of images from CT or MRI scans or from tissue sections or slides is highly complex. Currently, in radiology and in pathology only a tiny fraction (much less than one percent) of the regions to be examined is measured manually. Automatic analyses are starting to be used in pathology, especially since the introduction of tissue scanners. But automatic analyses of images created by tissue scanners today primarily imitate the manual work of the pathologist with the help of quantifications. Thus, tissue scanners do not improve the quality of the evaluations in any way, which patient profiles are able to achieve.

2. The system provides a communicable, understandable representation of the measured values. Currently, intelligent image analysis usually generates tables of measured values. The data in the tables are either too primitive, and thus do not account for the complexity of the image contents, or they correspond more to an automatic classification of the given image with a highly complex technical classification process that is nearly impossible to retrace. In addition, highly complex tables are not suitable for communication from the physician to the patient. Thus, measured values currently generated by intelligent image analysis either do not correspond to a true image-based patient profile due to the very narrow treatment of only a few aspects, or they are produced from a complex analysis which in the end yields an overall evaluation of the entire image which cannot be verified and is unsuitable for communication of how the final result has been achieved.

3. The system provides a verifiable, communicable, data-based presentation of the critical image regions. Image-based patient profiles (IPPs) illustrate the relationship of the measured values in the list to the corresponding image regions, which makes it easy for the physician to verify the automatic analysis. TPPs are a data-based illustration of evaluation results that can be communicated. For example, if the value for the calcification of the aorta, which was obtained from a CT scan, were to appear to be too high and to lie outside of the normal limits, system 10 relieves the physician from having to search in a cumbersome way along the aorta in the CT scan to locate the source of the abnormal value. When analyzing tissue sections, system 10 does not lose the connection between the data and the small areas within the tissue section from which the data originated.

4. The system provides a context-driven representation of the evaluation results. In the presentation of measured values, system 10 allows the user to select the context in which these results are viewed. In certain contexts, it makes sense to present certain values that, in another context, would only lead to confusion or would be superfluous. IPPs allow context to play an important role in the evaluation of measured values.

For example, the value ranges of certain characteristics of a patient may be considered normal for one person but not for another. In the simplest case, the determining factor is the age or the sex of the patient. In pathology, the normal range for the number of mitoses in children is certainly differently than for adults, and the size of the organs is also age dependent. This is one type of context that is derived from meta-data. Another form of context is provided by the purpose of the evaluation. In the context of staging, for example, the variation of values might be more important than the values themselves. In clinical monitoring, the values obtained during a previous examination represent the context for the values of a subsequent examination. System 10 defines personalized normal ranges for changes in the measured values. A third type of context might be given by an anticipated or proposed drug treatment. For a given proposed drug treatment the normal ranges of an IPP might be pre-defined and adjusted to the specific drug. In this case, the meaning of "normal" relates to the effectiveness of a drug for a specific disease and for a specific person. For a different drug treatment, the properties to be investigated might be the same, but the "normal" ranges for measured values might be different. For example, with cancer therapy using a particular drug, some values in the histological examinations are considered normal that would be considered abnormal in the context of another treatment. Whether measured values fall within various ranges can be used to decide which treatment should be used. In the simplest case, the treatment with the most values of the IPP being in the normal range would then be selected as the treatment of choice. The ranges for normal will in most cases be derived by experience, for example by finding correlations between values in the IPP and clinical data about the retrospective effectiveness of the drug being proposed.

5. The system links different patient profiles to each other and to other medical data, such as blood test results. System 10 presents different examination results to the physician in the form of lists of measured values, including all image-based examinations along with blood count values and other relevant patient data. This comprehensive collection of different patient profiles already presents a new form of computer-assisted diagnosis. It represents information for the doctor that is not available today. On the other hand, the medical doctor might be overwhelmed by the amount of information despite the fact that through the structure of the IPPs the complexity is already considerably reduced. In order to help the physician to understand the large amount of information, system 10 compiles particular patient profiles into a comprehensive profile. In this comprehensive profile, the system searches for patterns that are relevant for the patients' health. This could be done for all available values. The system will, however, treat the values that are out of the normal range as most important. The individual image-based patient profiles are lists evaluated using computer-assisted pattern recognition. As a result, any remarkable features within the individual IPPs are already marked. The remarkable features are logically connected by linking to each other within and between IPPs. The network of those marked values in linked IPPs form a new form of comprehensive patient profile. Unmarked values that are related to marked values can be added to this network to make the network even more comprehensive. In principle, however, all available values could be part of the network and relations between values as separate entities and the values themselves could be used to match the pattern of a patient to patterns that represent health-relevant comprehensive information like health risks, diagnosis suggestions, or treatment suggestions.

System 10 for generating image-based patient profiles performs a method having the following steps.

1. In a first step, system 10 analyzes the image data and creates a list of measured values. The image is measured comprehensively in multiple ways. In one embodiment, system 10 analyzes all anatomical objects in a radiological scan and measures the objects based on several criteria, including criteria that are not the particular focus of the examination. System 10 measures the size of the organs and their components, the density and brightness values of the objects, the textures in all image channels of the objects, and different shape properties of the objects (round, elongated, spined). The measured values are entered into a table.

A similar procedure is performed when measuring tissue sections. However, here there are different object types in tissue sections than in a radiological scan. For example, instead of measuring entire organs, different nucleus types and cell aggregations and glands are segmented and classified. But the principle is the same: a comprehensive measurement of many objects of different types. For both the pathological and the radiological examination, a complex list of measured values is created that is the first step toward the image-based patient profile.

2. The system evaluates the individual measured values, and the evaluations are represented graphically. Measured values that are evaluated as critical are enhanced graphically. In the simplest case, the evaluation is merely indicated by providing the value ranges that are considered normal with the given measured values in the table. Indicating or graphically representing the normal value range associated with a certain value drastically reduces the complexity of the interpretation of the results. The physician can concentrate on the measured values that are evaluated as critical. System 10 graphically enhances on the user interface those measured values that fall outside of normal limits. By clicking on a value or field that is close to the critical value and is made for this functionality, a previously prepared, written explanation of the medical relevance of the measured value can be read is presented to the physician.

For calculating or determining the normal ranges, the system can compare certain measured values with a histogram obtained from many similar measured values from healthy patients. If a measured value is high or low compared to the corresponding value in the histogram, then the value is evaluated to be critical. For example, the evaluation of a value x is inversely proportional to the value y of the corresponding standardized histogram at the place x. If insufficient statistical data are available, the histogram is evened out. As an alternative to presenting normal ranges, the histograms could be displayed directly.

3. The system allows the user to navigate from the measured values of the patient profile to the corresponding image regions. In order to communicate and verify the evaluated results, the physician will examine the corresponding image contents visually. A complete screening of the complex images would be too time consuming. Consequently, navigation through the image is carried out using the values from the table. If a value lies outside the normal limits, then by clicking on a field that is associated with the value, system 10 automatically navigates to the appropriate regions and displays the associated relevant image details.

Figure 6:
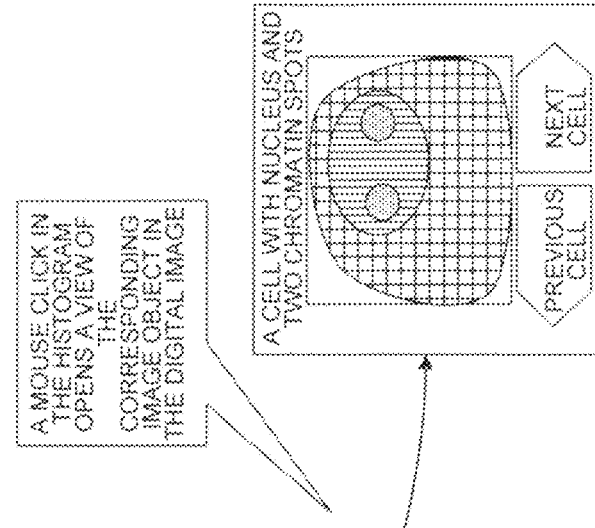
FIG. 6 illustrates navigating from a measured value to the region in a digital image that was the basis for the measured value.

FIG. 6 illustrates the navigation from a measured value to the region in the digital image that was the basis for the measured value. FIG. 6 shows an image-based patient profile 17 that graphically illustrates the number of chromatin spots per nucleus is the patient being diagnosed in comparison to the average value for healthy persons. When the user clicks on an abnormal measured value, system 10 displays the region of the digital image that produced the abnormal value.

The region associated with the largest deviation from the normal value is displayed first, and then the region with second largest deviation, etc. System 10 displays the image region either two dimensionally or three-dimensionally, or in a combined way. The image region can be represented with segmentation. The user of system 10 has the option of determining the size of the displayed image regions. A navigation from image to profile may be also beneficial for diagnosis. In this scenario, the user clicks on a segmented object; then the corresponding values in the patient profile are automatically visually marked. That enables the user to see immediately if the object in the image has to be considered normal or not normal.

4. The user chooses the context for representing the results. System 10 adapts the representation of the values of the patient profile and their normal limits. System 10 automatically chooses the context to represent some values based on metadata. For example, whether the patient is male or female and his/her age is determined from metadata. System 10 then chooses the types of values that are displayed as well as their normal limits. If a value is not relevant for a certain context, then this value and its associated normal limits are also not displayed. Displaying results in context applies to radiological views as well as to pathological views.

The user also has the option of choosing the context manually. For example, system 10 allows the user to select the values he wants explicitly, or the values he explicitly does not want. This selection corresponds in a certain sense to the definition of a context. In addition, various contexts are available as a choice in a list of options. For example, a radiologist can select "first evaluation" as the context, and thus examine the image-based patient profile for normalcy, and then use the context "staging" or "process control." In the second case, the changes compared to the previous results are displayed with the corresponding evaluations of these changed values or the corresponding normal limits for the changes. This corresponds then to a completely different representation.

There are also types of image profiles in which the indication of a normal range becomes appropriate at all only after a context is provided. Such context-driven profiles allow new information to be identified as compared with the conventional evaluation. A context driven profile could be used, for example, to diagnose a disease that has already been roughly diagnosed but remains to be described in a differentiated and specific way. Context driven profiles can be used for drug companion diagnosis in the field of personalized medicine, where the efficacy of a drug is pretested.

The context driven profiles are not used to determine whether a patient's measured values are within the normal limits for a healthy person because the patient has already been diagnosed as being sick, and the type of disease has been roughly diagnosed. Instead, the context driven profiles are used to specify the disease, to define what drug would be best for the treatment, and to determine the potential efficacy of the drug. For example, not all cancers are alike. A more specific diagnosis is called differential diagnosis, and when such a diagnosis is closely related to one drug it is called stratification. The context driven profiles are used to concentrate on the type of cancer as opposed to solely on the affected organ. Different cancer types can affect one and the same organ and require different treatments. The most prominent example of such examinations is the Her2 test in which a determination is made as to whether the Her2 protein is over-expressed in cell sections that have been stained with protein specificity. If the Her2 protein is over-expressed, then the cancer is a particularly aggressive type, and Herceptin, a drug tailored for this cancer, is usually administered. Conventionally, pathologists classify the stained tissue sections as "yes Herceptin," "possibly Herceptin" or "no Herceptin." It is currently assumed that these classifications from the point of view of the drug are equivalent to the classifications "Her2 strongly over-expressed," "Her2 moderately over-expressed," and "Her2 weakly or not over-expressed." Although many studies show that equating the two classification types may indeed be very helpful, an exact correlation does not exist. One case deals with the classification of the type of cancer, and the other with the classification of the efficacy of a drug. The study shown in FIGS. 2A and 2B shows that an image-based patient profile better measures both types of diagnostic statements than the simple classification described above.

In differentiating diseases or selecting an appropriate drug, there is a qualitative difference between simple classification and the image-based patient profiles (IPPs). Simple classification performed by a pathologist includes in the case of Her2-cancer four classes: 0, 1+ 2+ and 3+. In the 3+ case, for breast cancer and stomach cancer, Herceptin is administered. In the 2+ case, an additional test (for example, FISH) is performed, and in the 0 and 1+ cases, other therapy forms are chosen. An image-based patient profile, on the other hand, generates a value profile with the associated normal value ranges with respect to different contexts. If all of the values are in the green range, this corresponds to a 3+ classification, and Herceptin is administered. However, if all of the measured values are not in the green range, then the medical relevance of the values that lie outside of the normal limits is determined in connection with other information on the patient. An elevated value can have many different causes. The linking of the outlier value to a value from another profile may then provide an explanation for the deviation from the normal limits. Then a simple additional test that relates in a targeted way to the outlier value may provide the solution to the puzzle.

Such fine adjustments are not possible with a 3+ classification. A patient profile can be better optimized to clinical data than manual classifications that are based on a few or no measured values and that do not represent concrete, reproducible, number-based evaluations. Moreover, the manual classifications originate from subjectively chosen regions. The pathologist or treating physician can use the image-based patient profiles to quantify an evaluation in order to more precisely differentiate a disease or to select an appropriate drug without running the risk of losing a clear overview due to the large number of measured values.

5. The system interlinks different profiles in a knowledge-driven manner and generates a network of classifies objects. The knowledge-based network is then presented graphically to the physician in the form of a patient profile. All of the different patient profiles are integrated in a higher-level patient profile, called a meta patient profile (MPP). The meta patient profile includes all of the IPPs, the general patient data and the blood count values and possibly other types of patient data, such as demographic data in a standardized form.

FIG. 7 shows an exemplary meta patient profile 18. Meta patient profile 18 includes a tissue-based patient profile obtained from tissue slices, an image-based patient profile obtained from a CT scan and blood count values obtained from laboratory tests. The deviation of the measured values from the normal range are graphically depicted in FIG. 7 in two alternative representations. Meta patient profile 18 is displayed to the user of system 10 on graphical user interface 11.

For the purpose of standardization, the general patient data, such as blood pressure, age, hereditary risks, etc., is referred to as the general patient profile, and the blood count values and blood test results as the blood-based patient profile. The higher-level patient profile (MPP) is generated when all of the IPPs, the general patient profile and the blood-based patient profile are in a standardized form with hierarchical value lists plus the corresponding evaluations of the measured values. The compilation of these different patient profiles in a standardized form itself represents such a meta patient profile. The system displays an additional type of patient profile that is added to the meta-patient profile (MPP) and that is called the Super-MPP. On the graphical user interface, the Super-MPP depicts different risks for the existence of different diseases and the probability of success for the application of different specific treatments. The system searches for patterns in the patient data, including the patient profile lists that reflect those specific risks and success probabilities. The system indicates on the graphical user interface when a disease risk or a success probability for a specific treatment is high. The measured parameters with their values in the Super-MPP are then obtained from combinations of measured values from the lower-level patient profiles.

The system recognizes a mutual relation between patient profiles of different types, such as blood count values, tissue-based profiles or CT-based. For example, if the quantity of micro-calcifications in a tissue section is above the normal limit and simultaneously the calcification of the aorta is clearly above the limit value, and the blood cholesterol or sugar values are at elevated concentrations, then these values together are more informative than one value alone. There are two different components incorporated into the Super-MPP. One component is disease related, and the other is treatment related. Both kind of Super-MPP are meant to assist the attending physician to arrive at the correct conclusions with respect to the diagnosis on one hand and the correct treatment on the other hand. In the disease-related Super-MPP (Super-MPP-d), different measured values in the MPP are used to calculate a new value that represents a measure of the probability of the patient being healthy with respect to a specific disease. The strength of certain disease patterns is tested in this manner. Such values for different types of diseases are displayed in the Super-MPP-d. The system indicates on the graphical user interface when such values fall inside or outside the normal range of healthiness.

In the treatment-related Super-MPP (Super-MPP-t), different measured values in the MPP are taken to calculate a new value that represents the probability that the patient is responsive in a positive sense to a specific treatment. In this manner, the strength of certain responsiveness patterns with respect to specific treatments is tested. Such values are displayed in the Super-MPP-t for different types of treatments. The system indicates on the graphical user interface when such values fall inside or outside the normal range of positive responsiveness.

Figure 8:
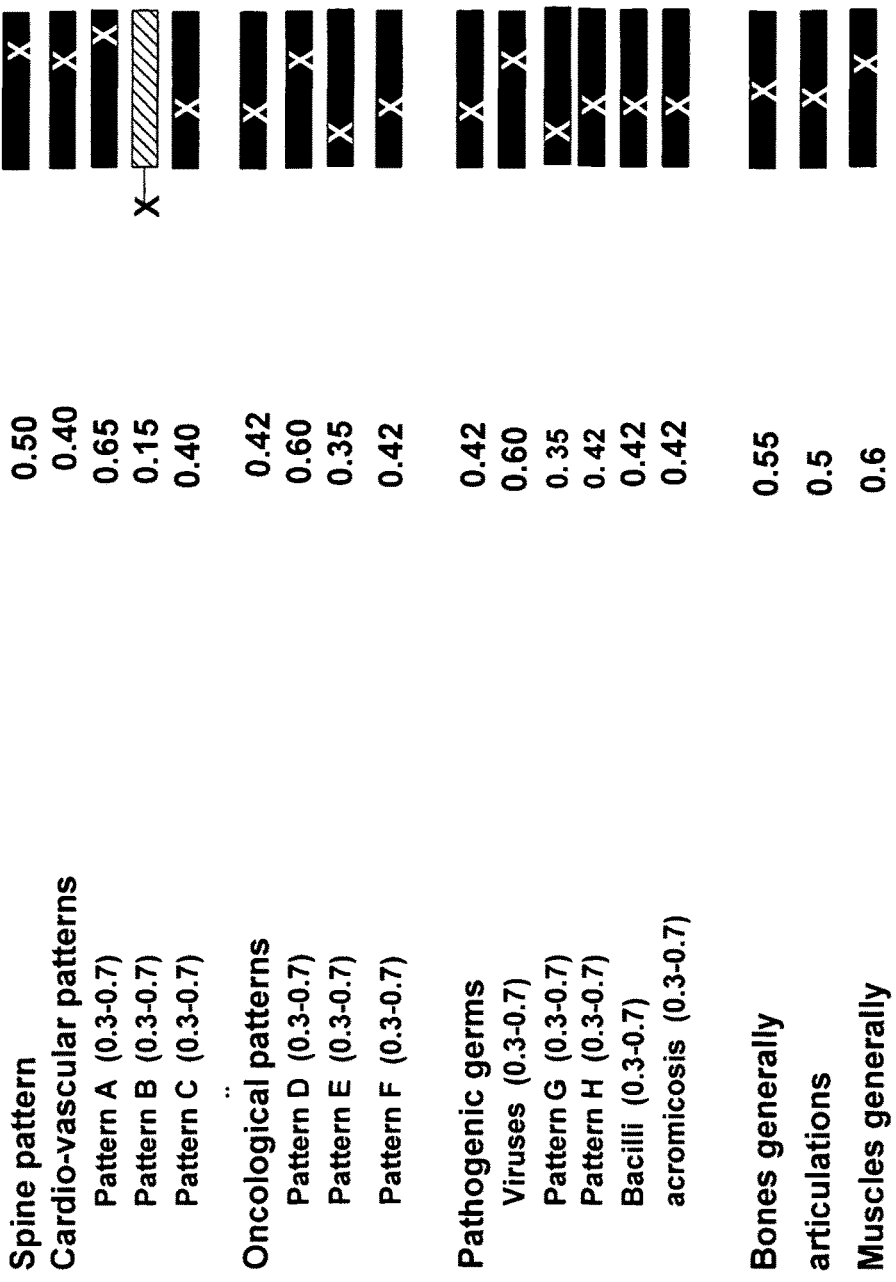
FIG. 8 shows an exemplary Super-Meta Patient Profile that depicts various patterns indicating the risk of the patient having cardiovascular disease.

FIG. 8 is an example of a Super-MPP-d. Various patterns A-H for cardiovascular disease risk are evaluated on the Super-MPP-d. Pattern A is derived from the calcification-related values described above. Pattern A is a formula that returns the risk of cardiovascular disease. The formula uses the quantity of micro-calcifications, $Q1$, the average density of calcifications in certain tissue sections, $Q2$, and the blood cholesterol or sugar values, $Q3$ and $Q4$ respectively, to calculate a value indicating the risk of cardiovascular disease. In the simplest case, these four different values are each multiplied by an individual factor, and the results are added to obtain one resulting value that reflects the risk. The value of pattern A (VA) is calculated as $VA=A*Q1+B*Q2+C*Q3+D*Q4$, where A, B, C, and D are constants that are derived from clinical studies. The normal ranges of this value are derived from clinical studies as well. Here it also becomes clear that the general patient data has an important correlation to the IPPs because the documented ingestion of drugs, the age, the weight, prior hereditary conditions, and an elevated blood pressure demonstrate a causal connection with the increased calcification levels represented in the IPPs.

The knowledge-based, intra- and inter-profile linkages of the individual measured values contribute an added value. Although the linkages can be made mentally by the physician with his specialty knowledge, there is a risk that the physician will fail to see particular patterns in the overall profile. Thus, system 10 performs a knowledge-driven search for such patterns in all the patient profiles, and presents this to the physician. System 10 possesses the data and the knowledge regarding the connections, recognizes pronounced correlations between this knowledge and the measured data, and communicates in the Super-MPP the detected correlations to the physician. The correlations are represented in the form of profiles, where the characterization of a pattern is quantified and represented jointly with a normal value range. A pattern can be represented by a formula containing several values from the meta patient profile, and the value that represents the fit to this pattern of an individual MPP is be calculated through a formula as shown above by calculating VA. This Super-MPP is prepared in the same form as the image patient profiles, the blood-based patient profile and the general patient profiles. In addition, normal ranges are displayed using the Super-MPP-values and by clicking on a field in the Super-MPP that is associated with a value outside a normal range. When the user clicks on a field, system 10 navigates the user to the data from which the value was calculated, in this case to the values from the MPP used in the formula for calculating the value. Both the Super-MPP-d and the Super-MPP-t operate by the same basic principles.

One list of measured parameters in the meta patient profile represents disease risks, and the values represent the strength of a pattern that is associated with this disease. This corresponds to a pattern match between comprehensive patient patterns and knowledge about patient patterns. The knowledge could be focused on patterns of healthy people (healthy match) or on patterns of sick people (disease match) with respect to a given disease. In the latter case, the evaluation of the value (represented by the strength of this pattern match) expresses the risk of the development and/or the presence of this disease. In the first case (healthy match), a good pattern match expresses for a given person a low risk of having a particular disease. The evaluation from statistical data with regard to the strengths of the given pattern are obtained from sick and healthy humans with clinical validation.

For standardization with respect to the other patient profiles, the meta patient profile possesses only a slightly different structure. The list of measured parameters in the meta patient profile represents the strength of a pattern that is associated with healthy people with respect to a disease (healthy match), first without an associated value. The measured value is then evaluated. It may be too high or too low. In this case, the risk for the development or presence of the disease is high. In the case that the measured value is within the "noncritical" value range, the risk for the development or presence of the disease is low. If the value is outside of this range, the value is marked as critical. For the disease match, the evaluation is reversed. In this case, there is probably no value that could be too low. In other words, the lower this value is, i.e., the lower the match to a disease is, the better for the patient. System 10 evaluates multiple patterns for each disease picture, which correspond to different causes of the same disease.

Figure 9:
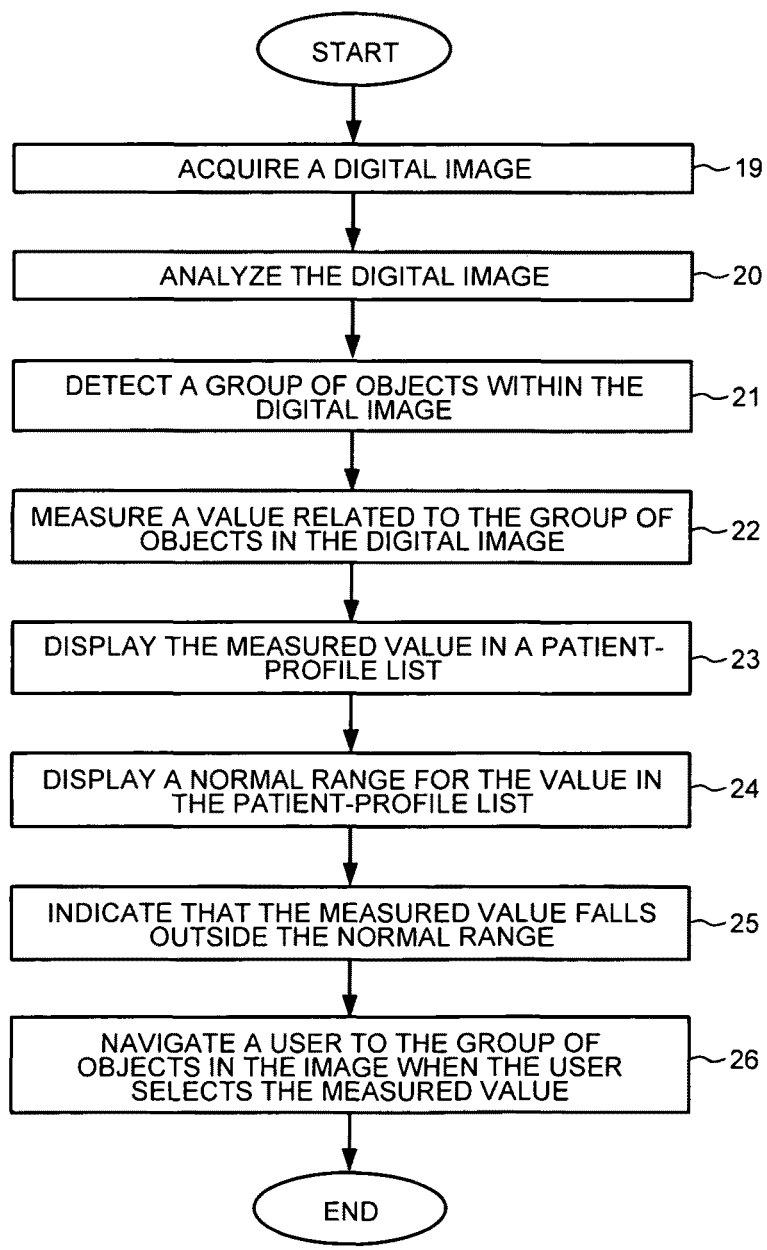
FIG. 9 is a flowchart of steps for generating an image-based patient profile.

FIG. 9 is a flowchart of a method by which system 10 generates image-based patient profiles.

In a first step 19, system 10 acquires digital images. For example, the digital images include digital images of tissue slices 12, digital images of CT scans 13 or digital images of blood. In addition, system 10 acquires blood values 14 from laboratory work as well as metadata relating to the patient. For example, the metadata includes that age, sex, weight, height and drug history of the patient.

In step 20, data analysis server 15 of system 10 analyzes the digital images using object-oriented pattern recognition.

In step 21, system 10 detects a group of objects in a digital image that was acquired in step 19 and analyzed in step 20. For example, system 10 detects a calcification on the aorta of the patient. The calcification is an object in a three-dimensional digital image of the aorta as shown in FIG. 5A. The aorta is another group of objects in the digital image.

In step 22, system 10 measures a value related to the group of objects in the digital image. For example, system 10 measures the volume of the calcification by counting voxels in the three-dimensional digital image. In another example, system 10 measures the two-dimensional area or diameter of the calcification and compares those measurements to the diameter of the aorta.

In step 23, system 10 displays the measured value in a patient-profile list. In another example, various measured values are displayed in the list shown in FIG. 7. The list is part of an image-based patient profile. For example, the measured value for the total volume of the largest lymph nodes is 130 cubic millimeters. System 10 generates a patient profile that includes the digital image and the list. For example, system 10 generates an image-based patient profile that includes, on demand, the digital image of FIG. 5A plus a list of measured values that includes the volume of the calcification.

In step 24, system 10 displays a normal range for the measured value. For example, system 10 graphically represents the normal range for the total volume of the largest lymph nodes as a rectangular box in the right column of FIG. 7.

In step 25, system 10 indicates to the user that the measured value falls outside the normal range for the value. For example, patient profile 18 of FIG. 7 is displayed on graphical user interface 11. Patient profile 18 graphically emphasizes that the total volume of the largest lymph nodes exceeds the normal value range for the total volume. The black area to the right of the rectangular box indicates that the lymph node volume for the patient falls outside the normal range of the lymph node volume of healthy patients.

In step 26, the user of system 10 is navigated to the group of objects in the digital image that correspond to the abnormal value when the user selects the measured value. For example, when the user selects the volume of the calcification on the aorta that falls outside the normal range, system 10 displays the calcification in three dimensions in FIG. 5A. The user is given the option to view the calcification in two dimensions in FIG. 5B. System 10 also displays FIG. 4 in which the calcification is highlighted within the context of the aorta in an anatomical model. FIG. 6 also illustrates how system 10 navigates the user to the objects in the digital images that were the basis for the abnormal values. The user is displayed a region in the digital image from the patient that shows a larger number of chromatin spots per nucleus than the average value for a healthy person.

System 10 notifies the user of abnormal values according to the degree by which the measured values deviate from the normal value ranges. System 10 first navigates the user to the images associated with the measured values with the largest deviation from normal.

Figure 10:
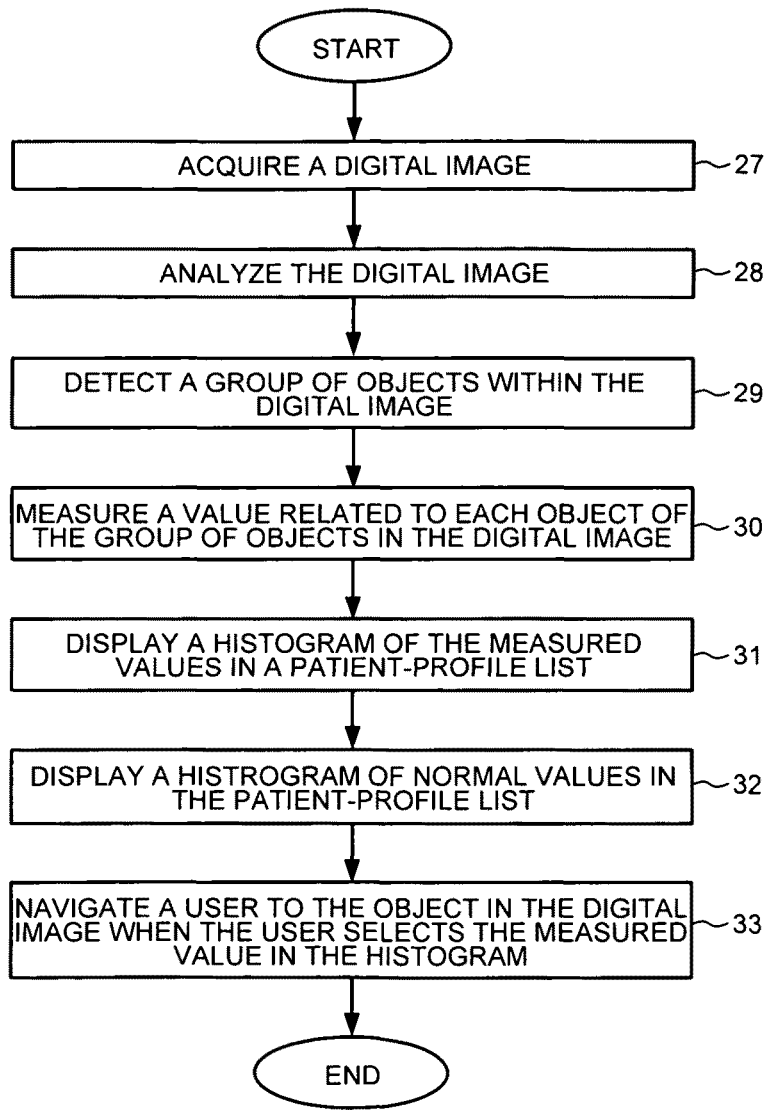
FIG. 10 is a flowchart of steps for generating an image-based patient profile with histograms such as those shown in FIG. 6.

FIG. 10 is a flowchart of a method by which system 10 generates an image-based patient profile with histograms such as that shown in FIG. 6.

In a step 27, system 10 acquires a digital image. In step 28, data analysis server 15 of system 10 analyzes the digital image using object-oriented pattern recognition. In step 29, system 10 detects a group of objects in the digital image. For example, system 10 detects a cell with a nucleus having two chromatin spots.

In step 30, system 10 measures a value related to each object of the group of objects in the digital image. For example, system 10 counts the number of chromatin spots inside each nucleus in the detected group of objects in the digital image.

In step 31, system 10 displays a histogram of the measured values in a patient-profile list. For example, system 10 displays a histogram showing the relative occurrence of nuclei having the indicated numbers of chromatin spots, such as the histogram above the line shown in FIG. 6.

In step 32, system 10 displays in the patient-profile list a histogram of the normal values for the values that were measured in step 30. For example, system 10 displays a histogram showing the relative occurrence in healthy tissue of nuclei having the indicated numbers of chromatin spots, such as the histogram below the line shown in FIG. 6.

In step 33, the user of system 10 is navigated to an object in the digital image that corresponds to the measured value selected by the user. For example, when the user selects nuclei having two chromatin spots by clicking on the appropriate bar in the histogram, system 10 successively displays all of the cells with nuclei having two chromatin spots. The user navigates to the various sections of the digital image in which the detected cells are located by clicking on "previous cell" or "next cell." In another aspect, system 10 navigates the user to a section in the digital image that contains the most cells having a larger number of chromatin spots per nucleus than the average value for a healthy person.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:
1. A method comprising:
analyzing a digital image;
detecting a group of objects in the image, wherein the group of objects includes normal anatomical objects and abnormal anatomical objects;
measuring a value related to the group of objects in the image;
displaying the measured value in a patient-profile list;
indicating that the measured value falls outside a normal range;
identifying the abnormal anatomical objects as potentially diseased based on the measured value falling outside the normal range;
navigating a user to a section of the digital image containing the abnormal anatomical objects from the group of objects when the user selects an area on a graphical user interface that is associated with the measured value that falls outside the normal range; and
displaying the abnormal anatomical objects on the graphical user interface.

2. The method of claim 1, wherein the group of objects are anatomical objects of a patient with a disease.

3. The method of claim 2, wherein the value is an average volume of the anatomical objects.

4. The method of claim 1, wherein the patient-profile list includes blood values of a patient.

5. The method of claim 1, wherein the measured value is a number of objects within the group of objects.

6. The method of claim 1, further comprising:
displaying the normal range as a histogram.

7. The method of claim 1, further comprising:
storing the age and sex of the patient; and
determining the normal range based on the age and sex of the patient.

8. The method of claim 1, further comprising:
measuring a second value related to a second group of objects in the image;
indicating that the second measured value falls outside a second normal range, wherein the second measured value is farther outside the second normal range than the measured value is outside the normal range; and
navigating the user to the second group of objects before the user is navigated to the group the objects.

9. The method of claim 1, wherein the navigating the user is performed by displaying the group of objects as an overlay on the digital image.

10. The method of claim 1, wherein the digital image is acquired by an optical microscope from a tissue sample.

11. The method of claim 1, wherein the digital image is acquired by a computer tomography device.

12. The method of claim 1, wherein the digital image is a time series of digital images.

13. The method of claim 1, further comprising:
analyzing digital images of a patient;
generating a plurality of patient-profile lists using measured values related to objects in the digital images;
defining a potential pattern that associates a particular disease with predetermined types of the measured values;
detecting that the measured values of the predetermined types fit the potential pattern associated with the particular disease; and
highlighting on a graphical user interface those measured values from the predetermined types that most contribute to the measured values fitting the potential pattern.

14. A system for generating image-based patient profiles, comprising:
a patient database, wherein a digital image is stored in the database;
a data analysis server that recognizes a group of anatomical objects in the digital image, wherein the data analysis server measures a value associated with the recognized group of anatomical objects, wherein the data analysis server evaluates the measured value as critical because the measured value falls outside a normal range and identifies the group of anatomical objects as potentially diseased abnormal anatomical objects, and wherein the data analysis server stores the measured value in the database; and
a graphical user interface on which the abnormal anatomical objects in the digital image, the measured value and the normal range are displayed.

15. The system of claim 14, wherein the system navigates a user to the abnormal anatomical objects in the image when the user selects a field on the graphical user interface that is associated with the measured value.

16. The system of claim 14, wherein the measured value is displayed in a context, and wherein the context represents a change of the measured value and similar measured values since a previous time step.

17. The system of claim 14, wherein an age and a sex of a patient are stored in the patient database, and wherein the data analysis server determines the normal range based on the age and the sex of the patient.

18. The system of claim 14, wherein the normal range is displayed on the graphical user interface as a histogram.

19. The system of claim 14, wherein the measured value is displayed in a context, wherein the data analysis server determines the normal range based on the context, and wherein the context is taken from the group consisting of: an assumed treatment of a patient, an assumed medication for the patient, and an assumed disease of the patient.

20. A method comprising:
analyzing digital images of a patient's anatomy;
detecting a plurality of anatomical objects in the digital images;
measuring values related to the plurality of anatomical objects;
defining a potential pattern that associates a particular disease to types of the measured values;
calculating a fit of the measured values to the potential pattern; and
indicating on a graphical user interface that the measured values related to anatomical objects of the patient's anatomy fit the potential pattern associated with the particular disease; and
displaying on the graphical user interface anatomical objects of the patient's anatomy that fit the potential pattern associated with the particular disease.

21. The method of claim 20, further comprising:
defining a plurality of potential patterns, wherein each of the plurality of potential patterns associates a set of measured values with a different disease.

22. The method of claim 20, further comprising:
highlighting on the graphical user interface the measured value that most contributes to the measured values fitting the potential pattern.

23. The method of claim 20, further comprising:
indicating that a measured value falls outside a normal range; and
navigating a user to a section of one of the digital images that contains an anatomical object related to the measured value that falls outside the normal range.

24. A method comprising:
analyzing a first digital image taken from a patient;
analyzing a second digital images taken from the patient;
detecting a first group of anatomical objects in the first digital image and a second group of anatomical objects in the second digital image;
measuring a first value related to the first group of anatomical objects;
measuring a second value related to the second group of anatomical objects;
calculating a third value using the first value and the second value, wherein the third value indicates the probability that the patient has a specific disease;
displaying the third value in a patient profile on a graphical user interface; and
indicating in the patient profile that the third value falls outside a normal range for healthy patients.

* * * * *